United States Patent [19]

Garnett

[11] 4,410,713

[45] Oct. 18, 1983

[54] PREPARATION OF FURAN COMPOUNDS

[75] Inventor: Donald I. Garnett, Hockessin, Del.

[73] Assignee: E. I. Du Pont de Nemours & Co., Wilmington, Del.

[21] Appl. No.: 372,559

[22] Filed: Apr. 28, 1982

[51] Int. Cl.$^3$ ............................................ C07D 307/36
[52] U.S. Cl. .................................... 549/505; 549/504; 549/506
[58] Field of Search ......................... 549/504, 505, 506

[56] References Cited

U.S. PATENT DOCUMENTS 4,172,838 10/1979 Garnett et al. ................. 260/346.11

OTHER PUBLICATIONS

Handy et al., J. Am. Chem. Soc., vol. 80, (1958), pp. 5306-5308.
Kondo et al., Tetrahedron Letters, 40, 3819, (1978).

*Primary Examiner*—Henry R. Jiles
*Assistant Examiner*—Bernard Dentz

[57] ABSTRACT

Process comprising contacting and reacting a substituted or unsubstituted diolefin polyperoxide, for example, butadienepolyperoxide, with an acidic aqueous medium containing cuprous and cupric ions and a water-soluble agent which forms a water-soluble complex with cuprous ions, and recovering furan or a substituted furan from the reaction mixture.

5 Claims, No Drawings

PREPARATION OF FURAN COMPOUNDS

DESCRIPTION

Technical Field

This invention relates to the preparation of furan and substituted furans.

Background

Furan is an industrially significant chemical compound in that it enjoys wide usage, not only directly, for example, in the production of resins, but also as an intermediate, for example, in the production of tetrahydrofuran. The art includes a variety of methods of synthesis of furan. It can be prepared from the pentosan component of corn cobs, oat hulls or rice hulls, via hydrolysis and dehydration to furfural which is subjected to the Cannizzaro reaction followed by decarboxylation. 1,3-Butadiene is also known in the art as a starting material in processes for the synthesis of furan. Such processes generally involve catalytic oxidation over a broad temperature range, either in the vapor phase at temperatures in excess of 375° C., or in the liquid or vapor phase at lower temperatures.

U.S. Pat. No. 4,172,838 includes reference to Japanese Patent Application Publication No. 52-77049 as a disclosure of a catalytic process carried out with 1,3-butadiene, either in the liquid or vapor phase, at 40°–150° C., using as the catalyst a palladium salt and a thallium or indium salt in an acidic aqueous medium. The U.S. patent also refers to Russian Patent 265119 as disclosing a similar process carried out at 60°–110° C., using a mixture of palladium chloride and cupric chloride in an acidic aqueous medium; alternatively, the reaction can be carried out using a mixture of cuprous chloride and cupric chloride in place of the palladium and cupric chlorides.

In the process of U.S. Pat. No. 4,172,838, the butadiene is contacted with an aqueous medium having a pH less than about 2 and containing iodine from elemental iodine or an iodine-containing compound, copper having an average oxidation state between 1 and 2, and a water-soluble solubilizing agent for cuprous ion, that is, an agent which forms a water-soluble complex with cuprious ion.

In microwave and nmr studies of the structure and the conformational isomerization of 3,6-dihydro-1,2-dioxin, also known as butadienemonoperoxide, Kondo, et al., Tetrahedron Letters, 40, 3819 (1978), disclose that the monoperoxide decomposes at room temperature to furan in the red-brass waveguide cell used for the studies, but is stable for one week at room temperature in a Pyrex ® tube. At about 210° C. in the Pyrex ® tube, the monoperoxide decomposes to furan within ten hours. The monoperoxide can be converted to furan in a gas phase reaction using cuprous chloride as the catalyst. Kondo, et al. also refer to Turner, et al., J. Org. Chem., 42, 1900 (1977), as disclosing the use of ferrous sulfate as the catalyst for such a reaction.

In all the aforesaid processes for preparing furan, to varying degrees, impurities may be present in the desired product. Removal of the impurities may be difficult and/or costly to achieve.

It is an object of this invention to provide a catalytic process for the production of furan and substituted furans. Another object is to provide such a process wherein the furan or substituted furan is produced with a minimum of impurities. Still another object is to provide such a process which is based on a butadiene derivative as the starting material. Other objects will become apparent hereinafter.

DISCLOSURE OF INVENTION

For further comprehension of the invention and of the objects and advantages thereof, reference may be made to the following description and to the appended claims in which the various novel features of the invention are more particularly set forth.

The invention resides in a catalytic process for producing furan and substituted furans at good conversions and yields and at practical rates of reaction. More particularly, the invention resides in the process wherein the polyperoxide of the diolefin of the formula

wherein each R is independently selected from H and $C_{1-4}$ alkyl, preferably methyl, and each $R^1$ is independently selected from H, halogen, preferably chloro, and $C_{1-4}$ alkyl, preferably methyl, is contacted with an acidic aqueous medium containing cuprous and cupric ions and a water-soluble agent which forms a water-soluble complex with cuprous ions.

Polyperoxides of the aforesaid diolefins can be prepared and separated from undesirable by-products and/or starting materials by means of known techniques.

Butadienepolyperoxide is well known in the art and can be prepared by oxidizing 1,3-butadiene with oxygen or air, such as disclosed in Japanese Kokai 53/68708 (1978), under 3 to 10 kg/cm² (about 300 to 1000 kPa) pressure at 60° to 100° C. in the presence of a solvent. The polymeric product consists of repeat units which suggest that both 1,4- and 1,2-addition of oxygen to the diene takes place, with the ratio of 1,4- to 1,2- being 1:1 to 1.5:1. Molecular weights of 700 to 3,000 are disclosed. A similar oxidation procedure, with product molecular weights of 700 to 850, is disclosed by Handy et al. in J. Am. Chem. Soc., 80, 5306 (1959). Similar processes which are carried out catalytically are disclosed in U.S. Pat. No. 2,879,306 and by Braithwaite et al. in Anal. Chem., 39, 1470 (1967). Disclosed therein as catalysts are azo-bis-isobutyronitrile, peroxides, such as benzoyl peroxide, hydroperoxides and diazothioethers. In general, the peroxidation reaction is slow to start. As disclosed by Handy et al., loc. cit., the peroxidation follows a typical autocatalytic curve and exhibits a pronounced induction period which can be minimized by a source of free radicals. Use of such free radical sources may provide problems in that residues of the free radical initiators usually are chemically attached to the polymeric butadieneperoxide as end groups. This problem can be circumvented by employing the procedure disclosed in U.S. Pat. No. 2,898,377 wherein preformed butadiene polyperoxide is used as the free radical source.

Other diolefin polyperoxides which are known in the art include the polyperoxides of 2,3-dimethyl-1,3-butadiene and 2-methyl-1,3-butadiene (isoprene). Both of these polyperoxides are disclosed by Bodendorf in Archiv. der Pharmazie, 271, 1 (1933) and isoprene polyperoxide is disclosed by Tilden in J. Chem. Soc., 45, 410 (1884).

By using the diolefin polyperoxide as the starting material in the process of the invention, the furan or substituted furan produced is of high quality, with a minimum of impurities. Moreover, no external source of oxygen or air is needed in the formation of the furan or substituted furan product and only a minimal amount of oxygen or air is required to sustain the catalyst composition. The polyperoxide can be used undiluted, or it can be first admixed with an inert carrier, such as nitrogen, carbon monoxide or carbon dioxide.

The aqueous medium used in the present process contains a copper redox catalyst, that is, a mixture of cuprous and cupric ions, and a solubilizing agent to aid in keeping cuprous ion in solution.

The metallic component of the catalyst of the invention is copper. The copper in the aqueous medium has an average oxidation state between 1 and 2, that is, the copper is a mixture of cuprous ion and cupric ion. Any copper compound soluble in the aqueous medium can be used, although copper halides such as the chlorides and bromides are preferred. Especially preferred is a mixture of cupric chloride and cuprous chloride even though either one alone can be added to the aqueous medium, in which event one can very quickly obtain a mixture of the two copper ions either through oxidation of cuprous to cupric or reduction of cupric to cuprous. The total copper concentration in the aqueous medium will usually be in the range of about 0.1–10 gram moles per liter, and normally about 0.5–3 grams moles per liter. Under preferred operating conditions, there will be a ratio of cupric ion to cuprous ion of 100:1 to 1:2, preferably 10:1 to 1:1. Illustrative copper compounds that can be used are halides of copper such as cupric chloride, cupric bromide, cuprous chloride, cuprous bromide and cuprous iodide; copper salts of organic acids, which may be carboxylic acids, such as acetic, propionic, pivalic, formic, succinic or adipic acids, fluorinated carboxylic acids, such as trifluoroacetic acid, sulfonic acids, such as methanesulfonic acid, benzenesulfonic acid and p-toluenesulfonic acid or fluorinated sulfonic acids, such as trifluoromethyl sulfonic acid; or salts of inorganic acids, such as cupric sulfate, cupric nitrate and cupric tetrafluoroborate.

In order to keep cuprous ions in solution, a solubilizing agent is used. A useful solubilizing agent is any inorganic or organic compound which is soluble in water and tends to form a water-soluble complex with cuprous ion. While alkali metal halides, alkaline earth metal halides, ammonium halides and halogen acids are preferred, other metal halides such as cobalt halides and iron halides, and organic solvents can also be used. By halides is meant the chlorides and bromides, and preferably the chlorides, of the aforesaid metals. Illustrative organic compounds include: organic nitriles, for example, aliphatic nitriles, such as acetonitrile, succinonitrile and propionitrile, and aromatic nitriles, such as benzonitrile; carboxylic acids, such as acetic acid; thiocyanates, such as sodium thiocyanate; and aliphatic amines, such as tetramethylethylenediamine, and their hydrochloride salts. It will be within the skill of the art to select a particular solubilizing agent and the appropriate amount to use. Especially preferred solubilizing agents are potassium chloride, sodium chloride, calcium chloride and ammonium chloride. The concentration of the solubilizing agent is typically in the range of about 0.01–5 gram moles per liter, preferably about 0.5–3 gram moles per liter.

The process of the invention can be carried out at a temperature in the range of about 50°–125° C., preferably 75°–105° C., and most preferably about 95°–103° C. Reaction pressures are typically in the range of about 0.1–10 atmospheres (10–1000 kPa), preferably about 1–3 atmospheres (100–300 kPa), and most preferably at atmospheric pressure (100 kPa). It is the partial pressure of the water, product furan or substituted furan, solvent and inert gas of the gas stream that determines the particular pressure used.

The starting material flow rate through the aqueous medium does not appear to be critical. As will be apparent, the flow rate should not be so fast as to give inadequate contact time between the starting material and aqueous medium or so slow as to enable the resulting furan or substituted furan product time to decompose or polymerize. It is preferred that the aqueous medium be agitated either mechanically or by good gas dispersion in the aqueous medium, and the reaction off-gases containing furan or substituted furan product be removed from the reaction vessel promptly. The optimum contact time between the starting material and aqueous medium depends on many factors and is readily determined by one skilled in the art.

Since copper compounds, for example, cupric chloride, may be very corrosive, the reactor for carrying out the process of the invention should be made of a material which is not corroded by the aqueous medium. Illustrative materials are glass or ceramic-lined metals, titanium, tantalum-clad metals, impregnated graphite tubes, and the like.

The following example adequately illustrates the process of the invention. In a typical experiment an acetic acid solution containing about 25% by weight butadienepolyperoxide was pumped into a 200 mL aqueous mixture of 40 g of cupric chloride, 28 g of cuprous chloride, 36 g of potassium chloride and 6 g of hydrochloric acid. The catalyst solution was maintained at 95° C. while nitrogen was sparged through a dip leg at 45 mL/min. The average oxidation potential of the catalyst was 0.387 volt vs. a standard calomel electrode. Furan was detected in the reaction off-gas by gas chromatography.

BEST MODE FOR CARRYING OUT THE INVENTION

As presently contemplated, the best mode for carrying out the invention process is illustrated by the aforesaid example. 1,3-Butadiene polyperoxide is a preferred starting material, as is isoprene polyperoxide.

INDUSTRIAL APPLICABILITY

The industrial applicability of the invention process for preparing furan and substituted furans is well known, as is evident from the background section of this specification.

Although preferred embodiments of the invention have been described above, it is to be understood that there is no intent to limit the invention to the precise constructions herein disclosed and that the right is reserved to all changes and modifications coming within the scope of the invention as defined in the appended claims.

I claim:

1. Process comprising contacting and reacting the polyperoxide of the diolefin of the formula

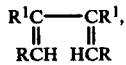

wherein each R is independently selected from H and $C_{1-4}$ alkyl and each $R^1$ is independently selected from H, halogen and $C_{1-4}$ alkyl, with an acidic aqueous medium containing cuprous and cupric ions and a water-soluble agent which forms a water-soluble complex with cuprous ions, and recovering a furan compound from the reaction mixture.

2. Process of claim 1 wherein the acidic aqueous medium contains hydrochloric acid and the water-soluble agent is potassium chloride.

3. Process of claim 1 wherein the diolefin is 1,3-butadiene.

4. Process of claim 1 which is carried out at 50°–125° C. at 0.1–10 atmospheres (10–1000 kPa) pressure.

5. Process of claim 4 which is carried out at 95°–103° C. at 1–3 atmospheres (100–300 kPa) pressure.

* * * * *